United States Patent [19]

Parkinson et al.

[11] 4,190,716
[45] Feb. 26, 1980

[54] POLYMERIC AGENT FOR RELEASING 5-AMINOSALICYLIC ACID OR ITS SALTS INTO THE GASTROINTESTINAL TRACT

[75] Inventors: Thomas M. Parkinson; Joseph P. Brown; Robert E. Wingard, Jr., all of Palo Alto, Calif.

[73] Assignee: Dynapol, Palo Alto, Calif.

[21] Appl. No.: 971,609

[22] Filed: Dec. 20, 1978

[51] Int. Cl.² .................. C08F 8/32; A61K 31/785; C08G 63/76; C08G 85/00
[52] U.S. Cl. .................. 525/334; 260/DIG. 47; 424/78; 424/81; 424/83; 528/172; 528/424; 525/56; 525/326; 525/327; 525/329; 525/330; 525/334; 525/336; 525/434; 525/437; 525/403; 525/523

[58] Field of Search .................. 424/78, 81, 83; 260/DIG. 47; 526/7, 13, 14, 16, 17, 21, 23; 528/172, 177, 273, 404, 424

[56] References Cited

U.S. PATENT DOCUMENTS 3,484,390   12/1969   Bauman et al. .................. 526/21

*Primary Examiner*—Stanford M. Levin
*Attorney, Agent, or Firm*—William H. Benz

[57] ABSTRACT

A generic polymeric agent for releasing 5-aminosalicylic acid or its salts is disclosed which comprises a nonabsorbable pharmacologically acceptable organic polymer backbone containing aromatic rings to which are covalently bonded via azo bonds a plurality of salicylic acid or salicylate salt groups. The azo bonds attach to the salicylates' 5-position carbon. The polymers undergo bacterial cleavage in the mammalian lower bowel to release 5-aminosalicylic acid and/or its salts.

10 Claims, No Drawings

POLYMERIC AGENT FOR RELEASING 5-AMINOSALICYLIC ACID OR ITS SALTS INTO THE GASTROINTESTINAL TRACT

BACKGROUND OF THE INVENTION

1. Field of the Invention

This invention concerns a new polymeric compound which when ingested by a mammal undergoes reaction with gastrointestinal bacteria to release a pharmacologically active agent.

2. The Prior Art

Salicylazosulfapyridine (SASP)

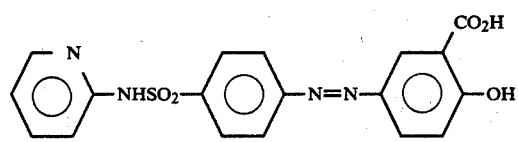

has been shown to be the most effective of the various sulfonamides in the treatment of ulcerative colitis and has been used clinically for over 30 years.

Upon oral ingestion, roughly 30% of the intact drug is directly absorbed from the upper small intestine. The remainder (~70%) suffers reductive azo cleavage in the caecum to give sulfapyridine (SP) and 5-aminosalicyclic acid (5-ASA).

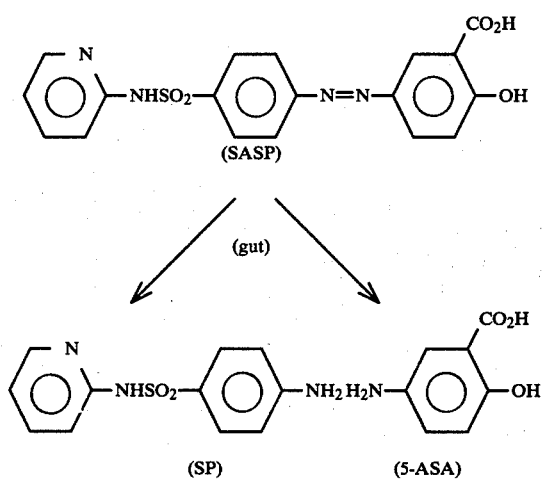

Absorbed SASP undergoes enterohepatic circulation and eventually is cleaved in the colon. Two to ten percent is excreted intact in urine. Sulfapyridine is absorbed, distributed throughout the body, and excreted in urine as glucuronide conjugates. Approximately 30% of the 5-ASA is absorbed from the colon; the remainder is excreted in the feces.

A limitation to the use of SASP is development of adverse side effects, which can be gastrointestinal (nausea, vomiting, anorexia, abdominal discomfort), hematologic (hemolytic anemia, leukopenia, transient reticulocytosis, pacytopenia), or generalized (headaches, vertigo, rashes, fever, cyanosis). In addition to these relatively common side effects, more serious adverse reactions have also been reported in the medical literature. These include agranulocytosis, toxic epidermal necrolysis, paresthesia, pancreatitis and pulmonary disease.

The toxic symptoms ascribed to SASP have been correlated with high serum concentrations of SP (>50 μg/ml) and decreased ability to acetylate SP. No correlation was observed with serum concentrations of SASP, SP metabolite, or 5-ASA.

The therapeutic mechanism of SASP could, in theory, be related to the intact drug or to either the antibacterial (SP) or antiinflammatory (5-ASA) cleavage product. In a recent study reported by P. Sharon et al., *Gastroenterology*, 75, 638–40 (1978), patients with ulcerative colitis were administered enemas of SASP and the two azo-cleavage products. About 75% of those who received SASP or 5-ASA improved, while only 38% of those who received SP showed a similar change. This significant difference, supported by sigmoidoscopy and biopsy findings, strongly suggests that 5-ASA is the therapeutic agent.

Assuming this hypothesis correct, we have reasoned that the toxic sulfapyridine portion of SASP merely serves to minimize intestinal absorption until 5-ASA can be generated by colonic bacterial reduction. A polymer leashed form of 5-ASA would be expected to be more effective than SASP for the site-specific release of 5-ASA in the colon. The potentional advantages of the polymeric drug include nonabsorption in the small intestine (i.e., controlled release) and elimination of side effects caused by SP.

STATEMENT OF THE INVENTION

We have now discovered a new polymeric compound which by its nature permits the prolonged administration of 5-ASA at a controlled rate while eliminating the release of undesired SP. This polymer compound is composed of a pharmacologically acceptable organic polymer backbone to which is attached a precursor of 5-ASA. The backbone has aromatic carbon atoms and is of a molecular size which precludes its absorption from the intestinal lumen. The 5-ASA precursor is an azolinked salicyclic acid or salicylate salt. These acid or salt groups are attached to the backbone through an azo linkage between a backbone aromatic carbon and a 5-position carbon on the salicyclic acid or salicylate. When the polymer passes through the mammalian G.I. tract, the azo linkages are bacterially cleaved releasing 5-ASA. The generation and absorption of cleavage products occurs in the lower bowel. The polymer itself is not absorbed.

DETAILED DESCRIPTION OF THE INVENTION

Definitions

In the present description and claims reference will be made to several terms which are expressly defined as follows.

The term "pharmacologically acceptable organic polymer backbone" shall mean a polymer backbone which is devoid of structural groups or atoms which are toxic or give rise to an adverse physiological response in mammals when ingested.

The term "average molecular weight" shall designate a mean molecular weight as determined by gel permeation chromatography comparison with known standard molecular weight polymers.

The term "molecular size which precludes absorption through the intestinal lumen" shall mean a molecular size that is larger than the maximum molecular size which can readily pass through the mammalian intestinal wall.

The term "recurring" is used to describe repeating units in a polymer chain. As so used, the term is intended to encompass not only the situation wherein a single unit repeats in a "homopolymer" structure, but also the situation wherein a unit appears in a polymer chain interspersed with other different units in a "copolymer" structure.

Structure of the Compounds

The compounds of this invention are polymeric in nature and comprise salicyclic acid groups (or salts thereof) bonded through their "5-carbon" position via azo links to aromatic carbons present in pharmacologically acceptable organic polymer backbones. Pictorially, such materials may be represented as shown in General Structural Formula I

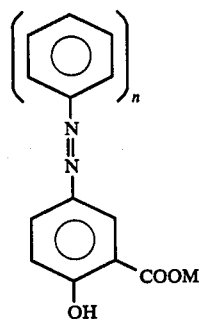

wherein M is hydrogen or a pharmacologically acceptable cation selected from among ammonium and the pharmacologically acceptable metal cations such as the nontoxic metal cations found in periods 3, 4 and 5, Group I, II, and VIII of the periodic Table of the Elements, i.e., cations of Na, K, Cu, Mg, Ca, Zn, Fe, Co, and Ni. Preferably, M is hydrogen, or cations of Na or K so that the group is present as a salicyclic acid group or as a sodium or potassium salicylate salt. Most preferably, M is sodium such that the group is a sodium salicylate group.

In pictorial representation

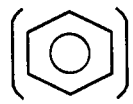     I.

represents a portion of an aromatic group-containing organic backbone from an aromatic carbon-atom of which extends an azo link and therefrom the salicyclic acid or salicylate group. "n" is an integer that is greater than 1.

The Polymeric Backbones

The aromatic-group-containing polymer backbone may take either of two structures. In one, the aromatic groups are present as groups pendant from an organic chain which links them together into the desired polymer backbone. Such a structure has n recurring

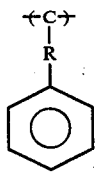

units wherein C is a portion of a nonmetabolizable organic chain linking the units together, n is an integer greater than 1 and R is a carbon to carbon single bond or a nonmetabolizable, pharmacologically acceptable organic linking group. Examples of such linking groups include amine links, sulfonamide links, ether links, ester links, amide links, carbamate links, alkyl links, and the like. Preferred as R are carbon-carbon single bonds and sulfonamide links.

The second backbone aromatic group configuration which can be employed in the present polymeric compounds has the aromatic groups as integral part of the backbone; such a structure has recurring arylene units, i.e., units. The azo links are attached to carbons of these arylene units. The backbones in either of these two configurations can be linear, branched or crosslinked so long as they present the requisite aromatic carbon groups required to affix the azo bonds in the final product. A number of examples of suitable polymeric backbones and an outline of the method of their use are given in a series of preferred embodiments. These are merely representative and are not to be construed as limiting the scope of the backbones useful in the practice of this invention. It is considered that the present invention involves the overall molecular system for releasing 5-aminosalicyclic acid, or its salts, and not merely a backbone. Accordingly, other art-known backbones which would provide the desired aromatic backbone carbons could be employed as well as the materials herein specifically embodied.

EMBODIMENT 1

Backbone: Polystyrene
Preparation:

-continued

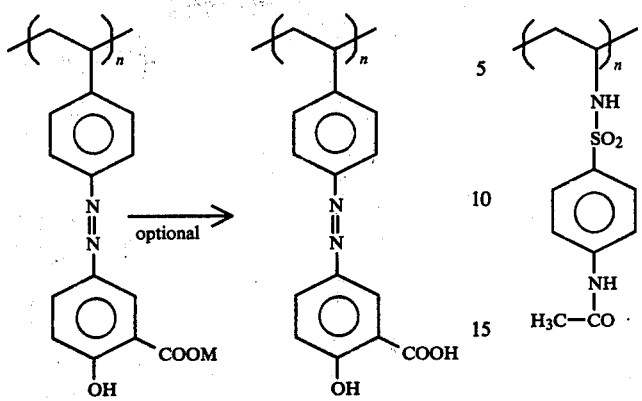

In this and all the other embodiments, only one polymer repeat unit is shown. This is done for simplicity. It will be appreciated that the several reactions are not all completely quantitative in yield. Accordingly, while the final product will have the unit shown as a recurring unit, it will also have other unreacted precursor units. In this embodiment, for example, the product would be expected to have four different units in an overall structure If, as is possible in accord with this invention, crosslinking groups were present, these would comprise a fifth recurring unit.

EMBODIMENT 2

Backbone: Poly(vinylamine)-Based Polysulfanilamide.

Preparation:

EMBODIMENTS 3, 4 AND 5

Backbone: The same as in Embodiment 2 except that the following units are copolymerized with the vinylamine units.

Embodiment 3—Acrylic acid (1–99 mol% basis number of total vinyl units).

Embodiment 4—Vinyl sulfonate (1–99 mole % basis number of total vinyl units).

Embodiment 5—Ethylene (1–99 mole % basis number of total vinyl units).

EMBODIMENT 6

Backbones: Poly(ethyleneimine)-Based Polysulfanilamide.

Preparation:

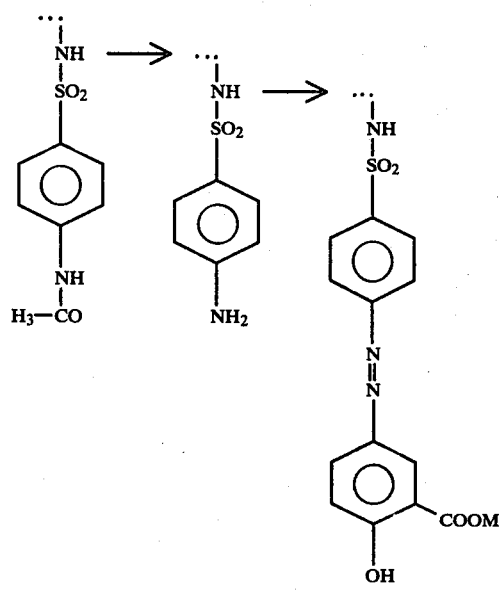

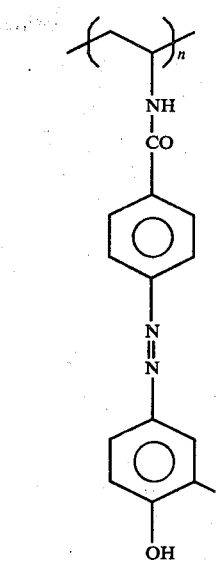

EMBODIMENTS 7, 8, 9 10 AND 11

Backbone: Polyvinylamine, its copolymers, shown in Embodiments 3, 4 and 5, and poly(ethyleneimine) following reaction with

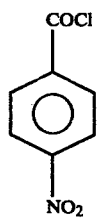

Representative Preparation:

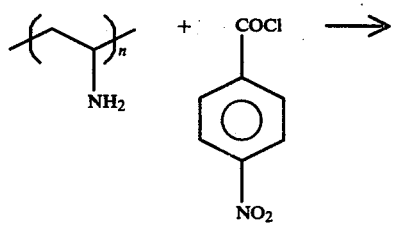

Aldrich Chemical
Cat. No. 11,220-8

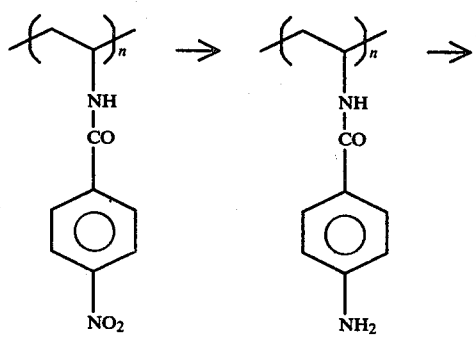

EMBODIMENTS 12, 13, 14, 15 AND 16

Backbone: Poly(vinylamine), its copolymers shown in Embodiments 3, 4 and 5, and poly(ethyleneimine) following reaction with

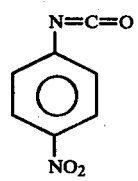

Representative preparation:

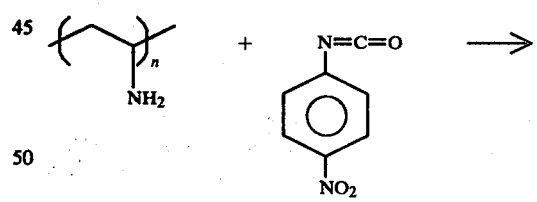

M. J. VanGelderen
Rec. Trav. Chim. Pays-Bas
52, 1969, (1933).

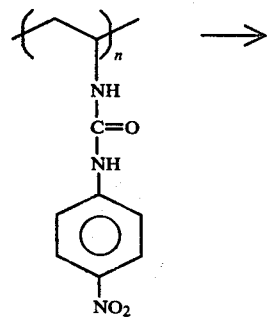

-continued
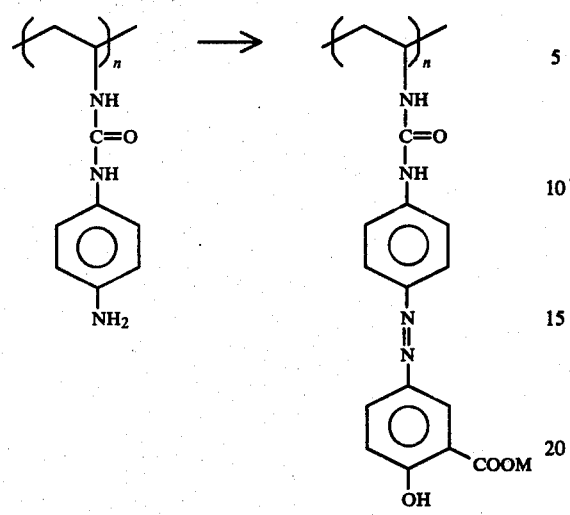
EMBODIMENTS 17, 18, 19, 20 AND 21
Backbone: Polyvinylamine, its copolymers shown in Embodiments 3, 4 and 5, and Poly(ethyleneimine) following reaction with
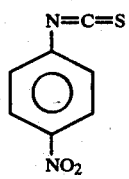
Representative Preparation:
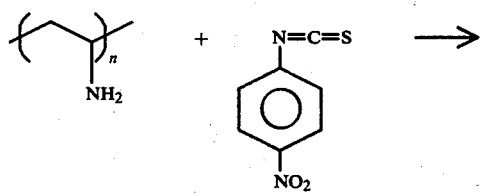
Eastman Organics Catalog No. 9940
-continued
EMBODIMENT 22
Backbone: Poly(N-methylvinylamine) following reaction with
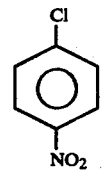
Preparation:
Aldrich, Cat. No. C5, 912-2

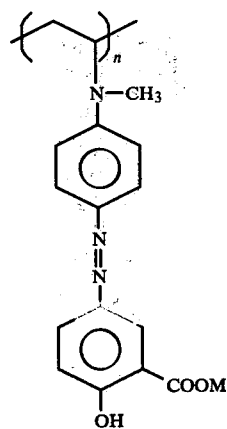

EMBODIMENT 23

Backbone use, instead of a homopolymer of N-methylvinylamine, a copolymer with from 1–99 mole % (basis number of N-methylvinylamine units) of ethylene, vinylsulfonate or acrylic acid.

EMBODIMENT 24

Backbone: Poly(vinyl alcohol) following reaction with

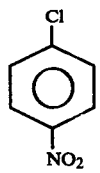

Preparation:

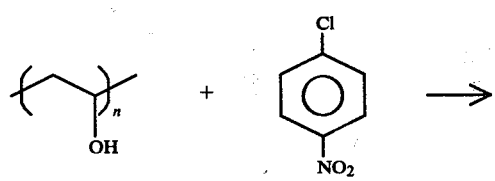

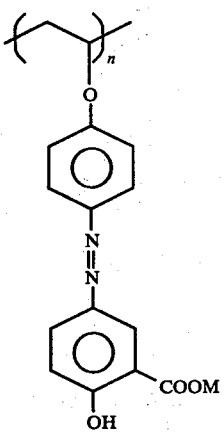

This same embodiment can also employ a copolymer of vinyl alcohol.

EMBODIMENT 25

Backbone: Poly(vinyl alcohol) (or copolymers of vinyl alcohol) following reaction with

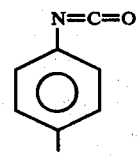

Preparation:

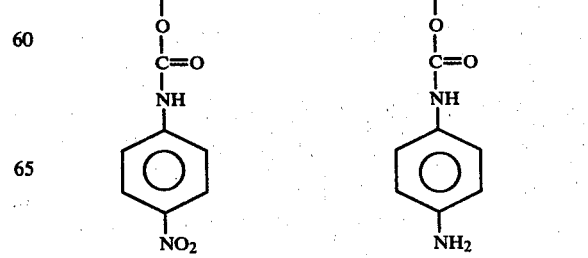

-continued
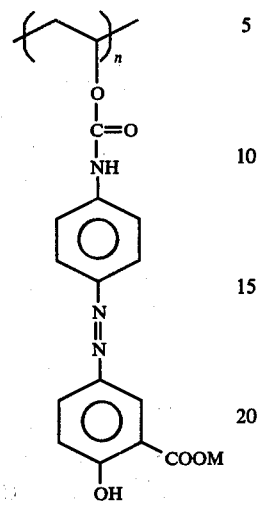
-continued
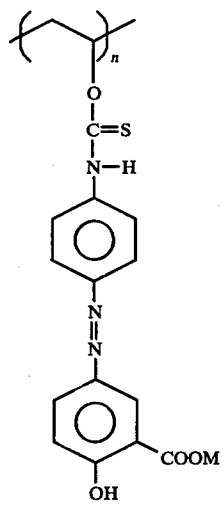
EMBODIMENT 26
Backbone: Poly(vinyl alcohol) or copolymers of vinyl alcohol following reaction with
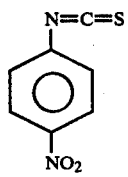
Preparation:
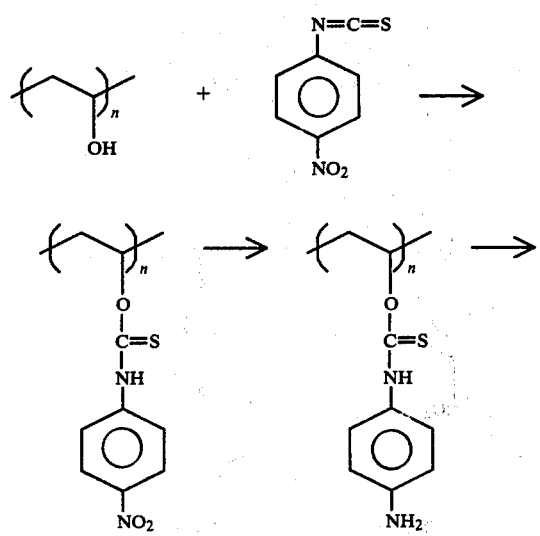
EMBODIMENT 27
Backbone: Poly(vinyl alcohol) or copolymers thereof following reaction with
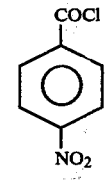
Preparation:
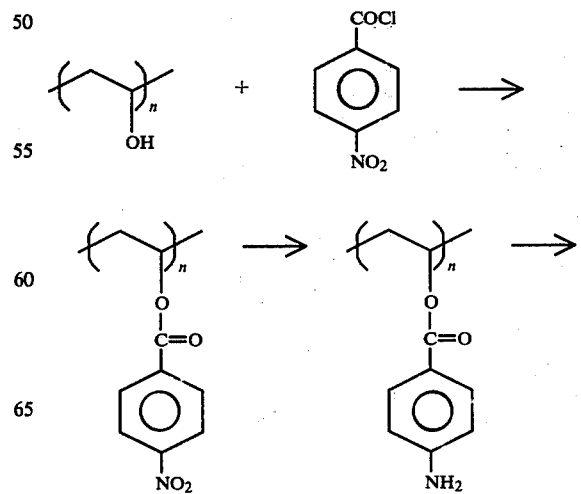

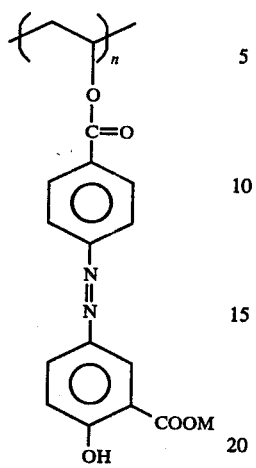
EMBODIMENT 28
Backbone: Poly(acryloyl chloride) following reaction with
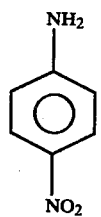
Preparation:
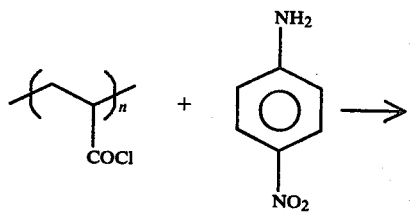
Aldrich, Cat. No. N985-3
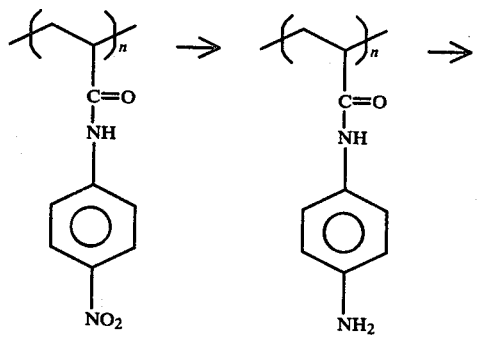
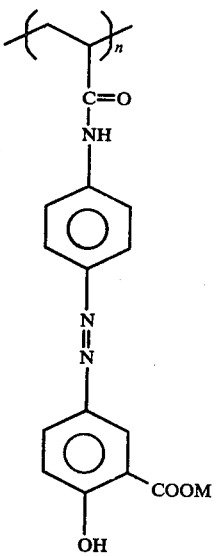
EMBODIMENT 29
Backbone: Poly(acryloyl chloride) following reaction with
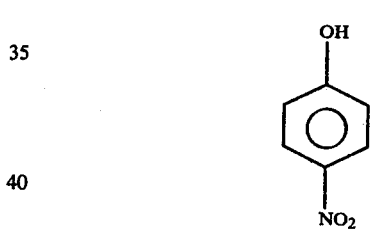
Preparation:
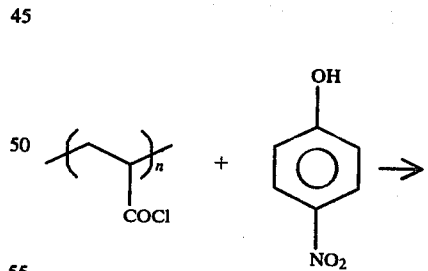
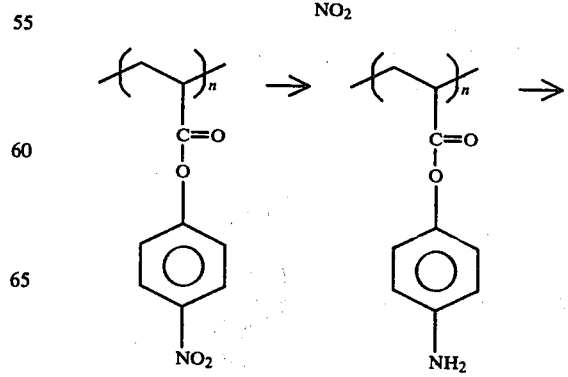

-continued

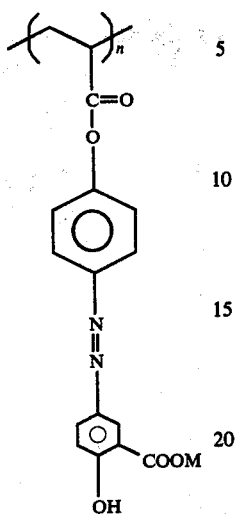

EMBODIMENT 30

Backbone: Poly(vinylisocyanate) following reaction with

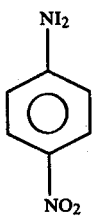

Preparation:

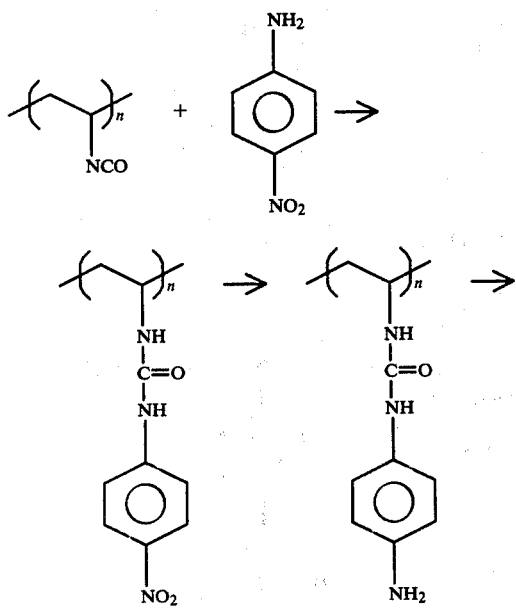

-continued

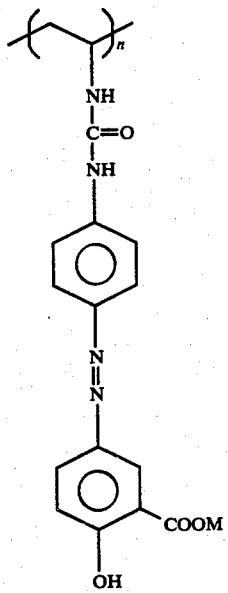

C. G. Overberger and C. J. Podsiadly, Macromol. Synth., Coll. Vol. I, John Wiley, N.Y., pp 473–476.

EMBODIMENT 31

Backbone: Poly(vinylisocyanate) following reaction with

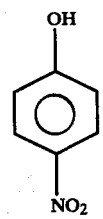

Preparation: This would be the same as the preparation shown in Embodiment 29 substituting poly(vinylisocyanate) as a starting material. The product would be

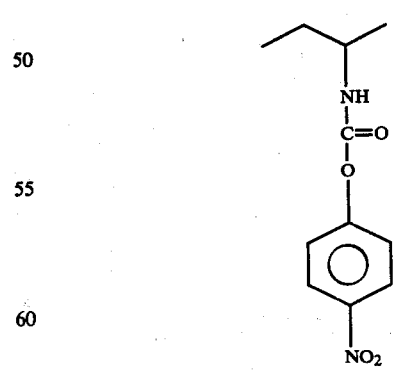

EMBODIMENT 32

Backbone: Poly(epichlorohydrin) following reaction with p-nitrophenol.
Preparation:

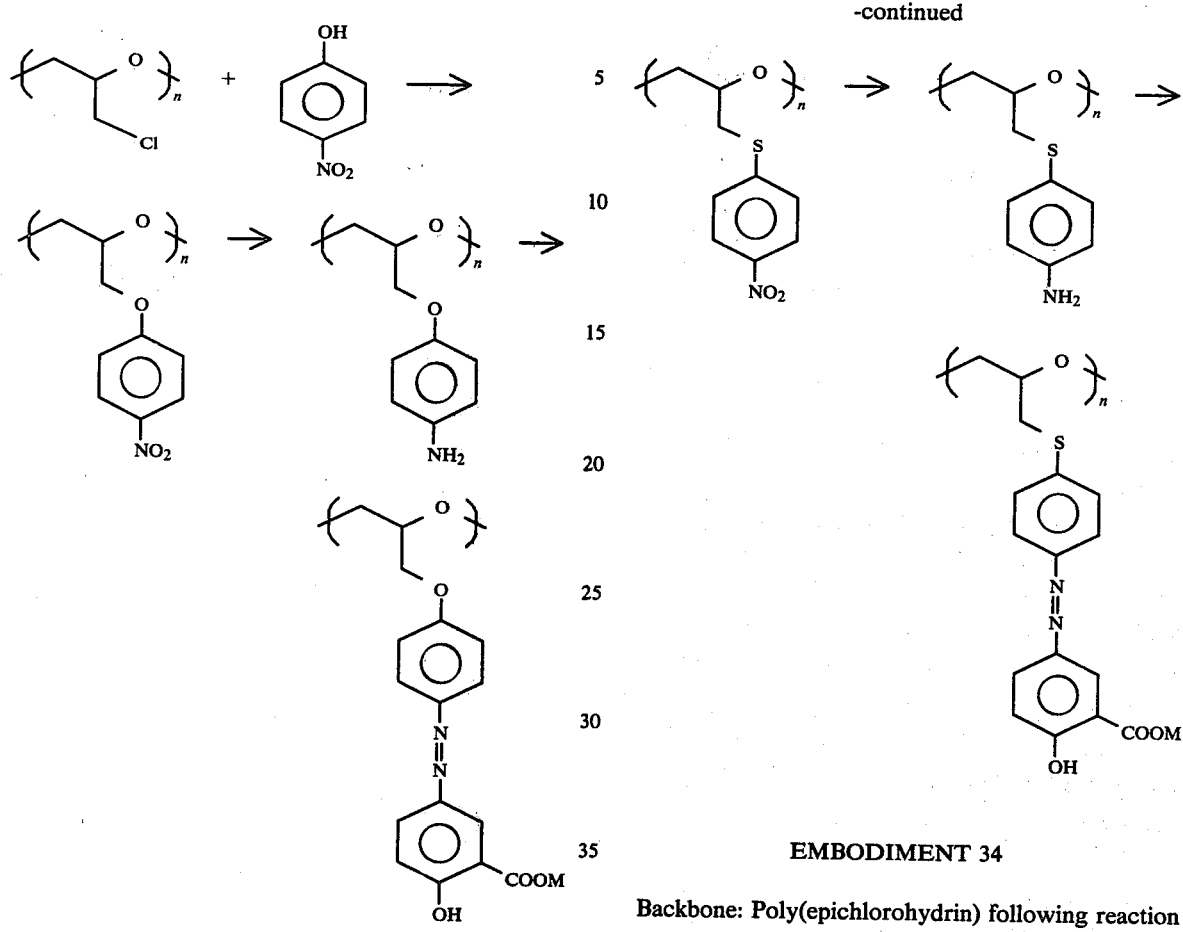
EMBODIMENT 33
Backbone: Poly(epichlorohydrin) following reaction with
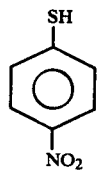
Preparation:
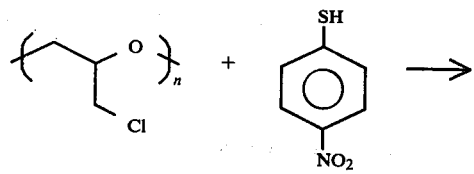
Aldrich,
Cat. No.
N2,720-9
EMBODIMENT 34
Backbone: Poly(epichlorohydrin) following reaction with
Preparation:
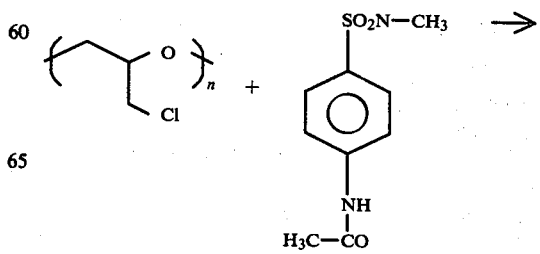

-continued
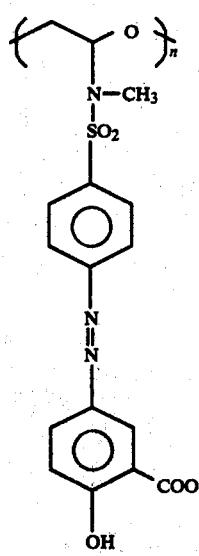
EMBODIMENT 35
Backbone: Poly(ethylene terephthalate)
Preparation:
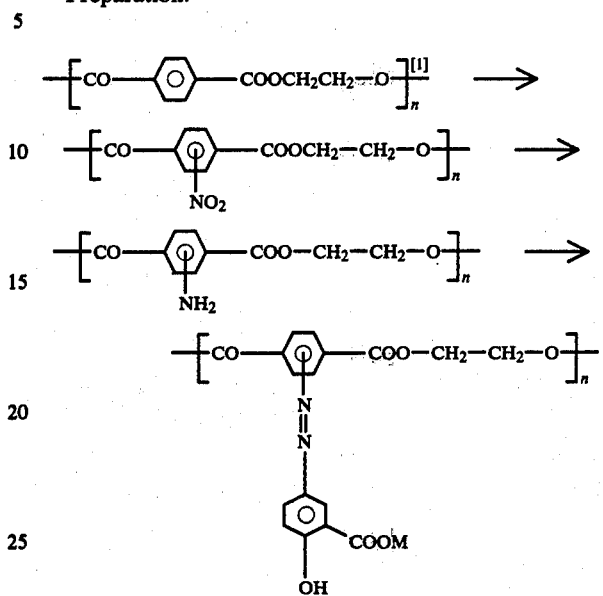
[1] C. G. Overberger, Macromol. Synth., 1, 17 (1963).
EMBODIMENT 36
Backbone: Bisphenol-A Polycarbonate [1].
Preparation:
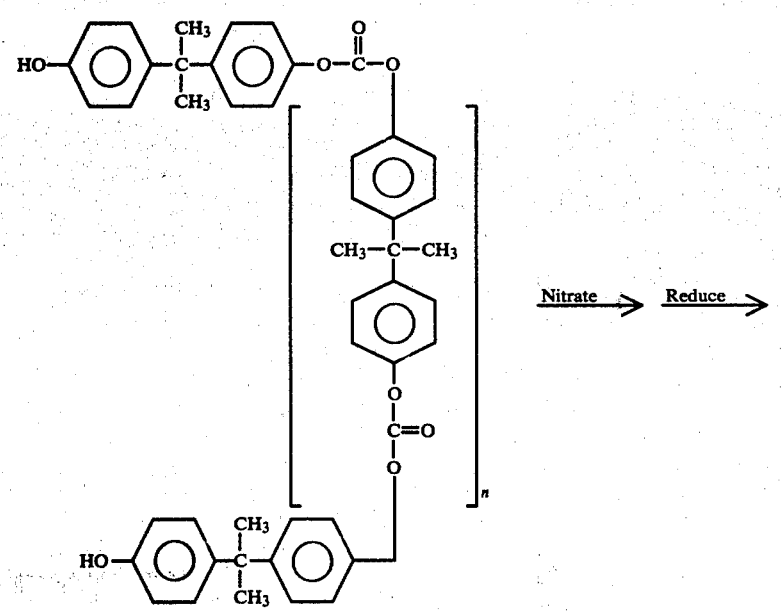

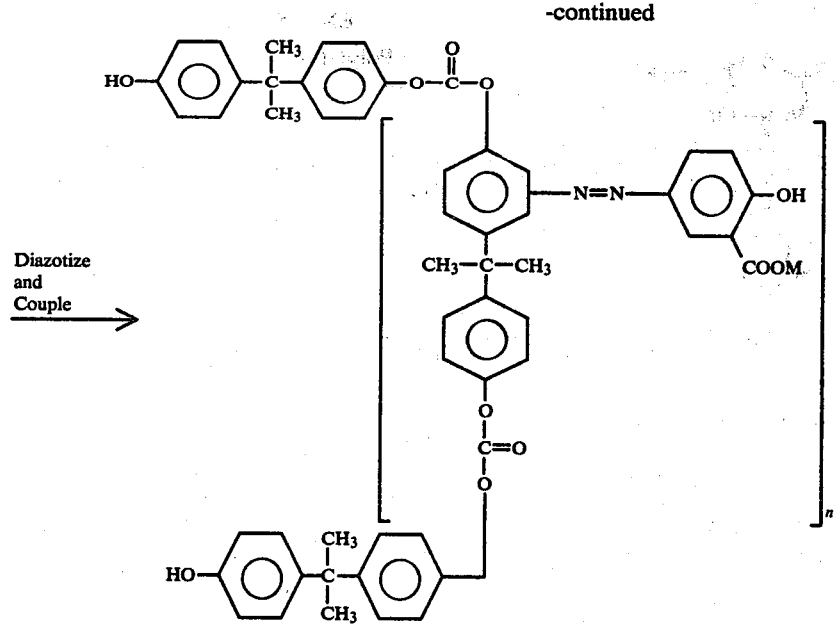
[1] C. G. Overberger, *Macromol. Synth.*, 1, 9 (1963).
EMBODIMENT 37
Backbone: Bisphenol A Polysulfone.
Preparation:
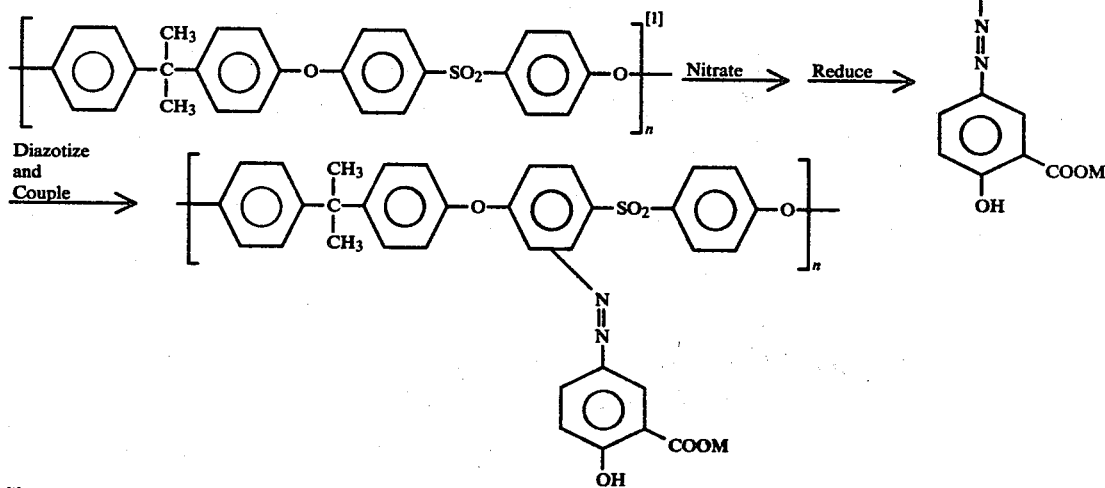
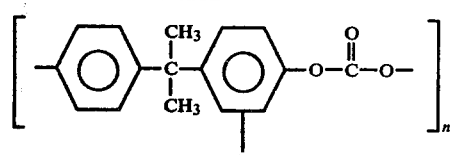
[1]Sorenson and Campbell, "Preparative Methods of Polymer Chemistry," 2nd Ed., Interscience, New York, N.Y., 1968, pp 181–2.
EMBODIMENT 38
Backbone: Poly[2,2-propanebis(4-phenyl carbonate)]
Preparation:
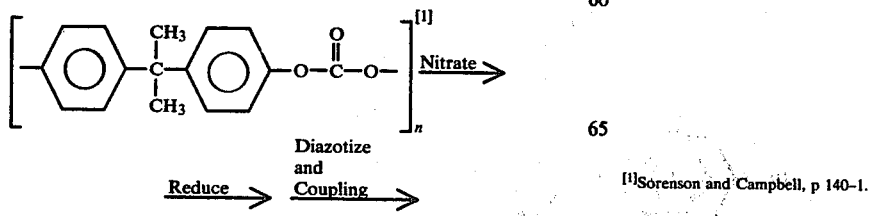
[1]Sorenson and Campbell, p 140–1.

Preferred Backbones

While there is no present reason to believe that certain backbones do a better or worse job of releasing the salicylates or salicylic acid into the gastrointestinal tract, some classes of backbones are preferred because of their ease of use in synthesis. For example, water-soluble backbones are generally easier to use, diazotize and couple than are water-insoluble backbones. Backbones based on alkylamine-group-containing polymers, especially those shown in Embodiments 2 through 6 are preferred. These materials are available and art-known, or based on available art-known precursors.

The molecular size of the backbone is important. If it is to accomplish its purpose of remaining nonabsorbable through the walls of the gastrointestinal tract, it must have a molecular weight above about 1000 daltons. Generally, this means that the backbone should have an average molecular weight of at least 1000 daltons with an average weight of from about 2000 to about 10,000,000 daltons being preferred and average molecular weights of from about 3,000 to about 1,000,000 daltons being more preferred and average molecular weights of from 5,000 to 500,000 being most preferred. If a polymer having a low average molecular weight is sought to be used, it may be of advantage to fractionate it, such as by fractional precipitation or ultrafiltration, so as to remove low polymers and oligomers having a molecular weight below about 1000 daltons. If a crosslinked polymer backbone is employed, an average molecular weight having orders of magnitude above those shown here would be realized, say in the many tens of millions.

These desired molecular weights also give rise to preferred value for n, the integer defining the number of units of salicylic acid on the polymer. As previously noted, n is at least 1. Preferably, n is from 5 to 40,000, with values of from 10 to 10,000 being more preferred.

The degree of substitution, that is the fraction of backbone aromatic rings that are substituted with azo-linked salicylic acid groups can vary. No advantage is seen in very low substitution as it means that exaggerated amounts of backbone need be consumed. Substitutions of from about 10 to 100% are generally preferred. As a rule, only one azo group attaches to a single backbone aromatic ring. It is preferred if the number of backbone aromatic rings is 10 or greater and the number of salicylate units (n) is 5 or greater. More preferably, the number of rings is from 10 to 30,000 while n is from 5 to 20,000. Most preferably, the number of rings is 10 to 20,000 and n is 10 to 10,000.

Preparative Methods

In the illustrative embodiments, a variety of preparative methods are briefly set forth. The examples describe several methods in detail. In this section a general expansion of the methods of the illustrative embodiment is provided.

A. In Embodiments 1 and in many later embodiments, an azo group is introduced by (1) nitrating an aromatic ring, (2) reducing the resulting aromatic nitro group to an amine. In all embodiment diazotizing and coupling are shown. The nitration of aromatic rings may typically be carried out by standard methods such as those found in the C. A. Buehler and D. E. Pearson, "Survey of Organic Syntheses," Vol. I, Wiley-Interscience, New York, N.Y., 1970, pp 980–991. Preferred methods include the use of (1) $KNO_3$ in 96% $H_2SO_4$, (2) mixed acid ($HNO_3$–$H_2SO_4$), and (3) red fuming nitric acid.

The reduction of these nitro groups to amines may be conducted using standard procedures such as those found in C. A. Buehler and D. C. Pearson, "Survey of Organic Syntheses," Vol. I, Wiley-Interscience, New York, N.Y., 1970, pp 413–417. Preferred methods include (1) treatment with $Na_2S$, (2) treatment with sodium dithionile ($Na_2S_2O_4$), (3) treatment with metal (e.g., Fe, Sn, or Zn) and acid, (4) catalytic reduction (e.g., 5%, Pd on C and $H_2$), and (5) treatment with phenylhydrazine.

The diazotization of the aromatic amine groups is carried out on an acidic solution or suspension of the polymers. The solution or suspension is contacted with a slight excess of a nitrite, such as sodium nitrite, potassium nitrite or the like at low temperatures (0° C. to about 35° C.). The diazotization is generally very quick, requiring only a minute or two so that reaction times of from 0.1 minute to about 2 hours may be used.

The coupling of the salicylic acid group is effected promptly after the amines are diazotized. The solution or suspension of diazotized polymer is mixed with a solution of salicylic acid at low temperature (0° C. to about 35° C., preferably 0° C. to 10° C.). Some excess of salicylic acid is generally employed. The pH is maintained basic, such as above about pH 10, preferably pH 13–13.5 by addition of base, such as KOH or HaOH. The mixing may be done stepwise. The time required for coupling is from about 0.25 hour to about 5 hours with times of 1 to 2 hours generally giving good results.

B. It has been pointed out that the salicylic acid group may be present as a free acid or as a salt. If the acid is desired, the coupling product is acidified with a strong acid such as hydrochloric acid or the like. If a salt is desired, acidification need not be carried out.

C. In preferred Embodiments 2-6, an alkylamine is converted into a sulfonamide group as the reqired pendant aromatic ring is introduced. This step is well effected by a "Schotten-Baumann" type reaction wherein the alkyl amine is contacted with an aromatic compound containing an amine precursor functionality and a sulfonyl chloride functionality

at relatively low temperatures (40° C. or less) and a pH of about 9–10. A typical reaction employs an aqueous reaction solvent, preferably also containing some water-miscible polar organic solvent such as tetrahydrofuran, dioxane, dimethoxyethane, dig lyme, isopropanol or t-butanol and vigorous agitation.

Suitable aromatic compounds for use herein are N-acetylsulfanilyl chloride,

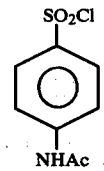

and the like.

The concentration of polyamine in the solution should be maintained at from about 1% to about 20%.

As a rule, the aromatic compound should be added gradually over a period of at least about 0.25 hours. During this addition, the pH should be monitored and maintained between about pH 9 and 10. After the addition is completed, the pH may suitably be raised somewhat, such as to 10-11, and the mixture stirred for an additional 0.5 to 4 hours. The reaction which occurs is as follows in the case where N-acetylsulfanilyl chloride is employed:

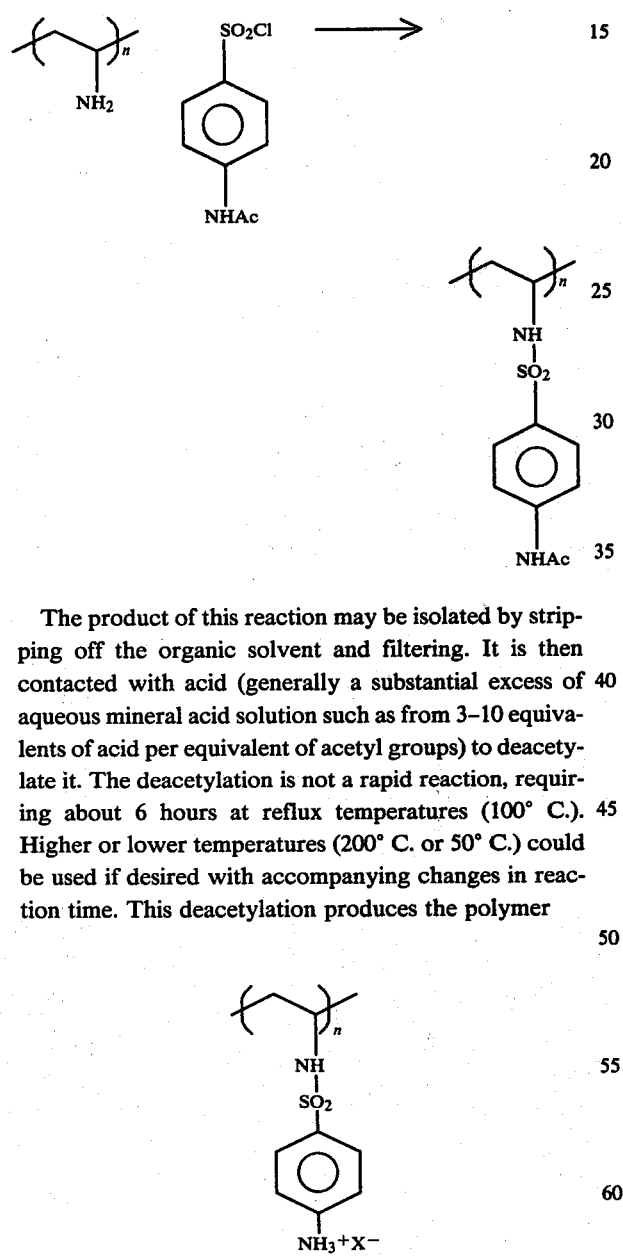

The product of this reaction may be isolated by stripping off the organic solvent and filtering. It is then contacted with acid (generally a substantial excess of aqueous mineral acid solution such as from 3-10 equivalents of acid per equivalent of acetyl groups) to deacetylate it. The deacetylation is not a rapid reaction, requiring about 6 hours at reflux temperatures (100° C.). Higher or lower temperatures (200° C. or 50° C.) could be used if desired with accompanying changes in reaction time. This deacetylation produces the polymer wherein X⁻ is the anion corresponding to the mineral acid employed.

D. In Embodiments 7-11, the condensation of a polymeric amine with

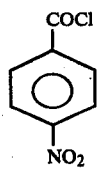

is shown. This reaction may be carried out by contacting the polyamine with an excess of the acid chloride in aqueous media of alkaline pH at moderate temperatures (roughly 0°-35° C.) for 0.5-3 hours.

E. In Embodiments 12-21 and 25 and 26, coupling reactions with

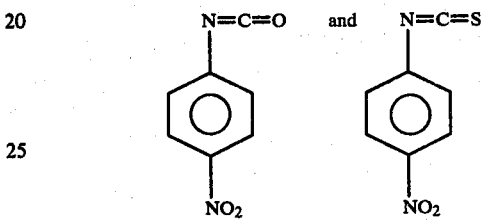

are shown. The polyamine couplings may be conducted with an excess of the isocyanate or the isothiocyanate in aqueous media at moderate temperatures (about 0°-35° C.) for 0.5-3.0 hours. The coupling reactions with polyvinyl alcohol are best conducted neat or in an inert solvent (e.g., dimethyl sulfoxide or hexamethylphosphoramide). These reactions also require higher temperatures and longer contact times.

Use of the Salicylic Acid Polymers

The compounds of this invention have the property of undergoing bacterial cleavage of their azo bonds at conditions found in the gastrointestinal tract of mammals. The t-aminosalicylic acid molecular fragment so liberated is of a size that is absorbed through the walls of the gastrointestinal tract and thus permits 5-aminosalicylic acid to enter the mammalian bloodstream. As noted in the example, this does in fact occur. Based on the art's teachings of the pharmacological desirability of administering 5-aminosalicylic acid free of absorbable coproducts, administration of this compound clearly should have a desirable therapeutic effect. In such use, a therapeutically effective dose would be used, such as, for example, a dosage essentially equal in moles to the molar dosage effective with salicylazosulfapyridine (SASP).

The invention will be further described by the following example. This is intended solely to exemplify the invention and is not to be construed as limiting its scope.

EXAMPLE

Reaction Scheme:

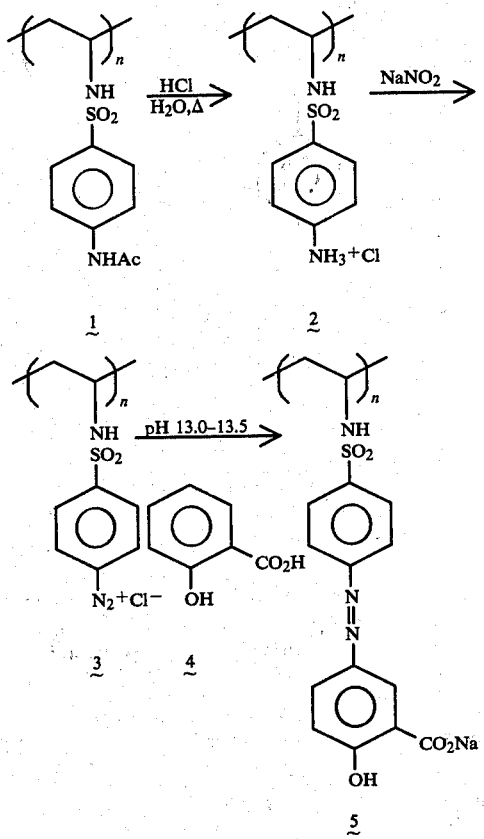

A. Hydrolysis

A 100-ml, 3-neck flask, equipped with overhead stirrer and oil bath, was charged with 4.00 g (16.7 mmol) of polymer 1 (prepared from polyvinylamine hydrochloride of mol wt $3\times10^4$ by the procedure of Gless et al., U.S. Pat. No. 4,018,826), 33 ml of $H_2O$, and 8.80 ml (106 mmol) of 12 N HCl. The mixture was stirred vigorously at reflux for 6 hours to effect hydrolysis.

B. Diazotization and Coupling

The solution of polymeric sulfanilamide prepared above was converted to diazonium salt 3 by the rapid addition of 4.00 ml (20.0 mmol) of 5 N $NaNO_2$ solution via syringe (25° C., vigorous stirring). A positive KI starch test was obtained after 5 minutes.

A 600-ml beaker, fitted with magnetic stir bar, thermometer, pH probe, and 50-ml dropping funnel, was charged with 6.9 g (50.1 mmol) of salicylic acid (4), 200 ml of $H_2O$, and 12.5 ml (100 mmol) of 8 N NaOH. After stirring for 5 minutes, ice was added to the clear solution to lower the temperature to 10° C. and the addition of the diazonium salt via the dropping funnel) was begun.

Throughout the addition (45 min) the pH was maintained at 13.0–13.5 by the addition of 8 N NaOH (16.5 ml added), and the temperature maintained at 10°–20° C. by the addition of ice. The solution was stirred for one hour at ambient temperature and then neutralized (to pH 7) by the addition of 12 N HCl.

The salts and low molecular weight impurities were removed by bag dialysis (regenerated cellulose, average pore radius 24 Å, estimated molecular weight cutoff $2\times10^4$) against 0.05% saline solution for 168 hours (dialysate changed every 12 hours), followed by dialysis against pure $H_2O$ for 12 hours. The solution was centrifuged (5000 rpm $\times$ 90 min) to remove a small amount of crosslinked product, passed through an 8.0$\mu$ filter, and freeze dried to afford 5.65 g (91.7%) of polymeric drug 5 as solid: UV $\lambda_{max}$ ($H_2O$) 354 nm, a 44.2 (g/$L^{-1}cm^{-1}$. Anal. Calcd for $(C_{15}H_{12}N_3O_5SNa \cdot 2H_2O)_n$: C,44.44;H,4.02;N,10.37; S,7.91. Found: C,44.40;H,4.06;N,10.13;S,7.84.

C. Biological Tests

A series of in vitro and in vivo tests were conducted to demonstrate the behavior of the polymer product of Part B in the mammalian gastrointestinal tract.

The polymer product of Part B was contacted with rat lower bowel microflora in vitro and observes to undergo anaerobic reductive azo bond cleavage.

Cecal contents were removed from freshly sacrificed rat, suspended in VPI diluent and filtered under $N_2$. Five ml of the cell suspension (1 g fresh weight/25 ml) were added to 0.05 ml of 20 w% α-D-glucose, 0.5 ml 1.0 mM benzylviologen or distilled water and 2.5 ml of a solution of the polymer product of Part B in screw cap tubes. The tubes were gassed for a few minutes with $N_2$, sealed and incubated for 48 hours at 35° C. Samples were removed from the tubes periodically by hypodermic needle and syringe in order to measure azo reduction by decrease in visible absorbance at the $\lambda_{max}$. It was observed that in the absence of the redox mediator dye benzylbiologen, the polymeric compound is azo-bond reduced about 50% in 6 hours. In the presence of benzylviologen the the polymers' azo bonds are completely reduced by the bacteria in less than two hours.

The polymer of Part B was fed to acclimated female Simonsen rats (200–300 g). Nonfasted rats were dosed with 20 mg of the polymer (ca. 40 $\mu$mole of 5-ASA as an aqueous solution. For purposes of comparison, a control group was dosed with ca. 40 $\mu$mole of potential 5-ASA in the form of an aqueous suspension of SASP. Blood, urine and fecal specimens were collected at regular intervals from both groups.

The results of this study showed that SASP and the polymer product had similar patterns of 5-ASA cleavage product delivery to the lower bowel contents, blood serum and urine. No SP delivery was observed with the polymer. Hence, it is considered that the polymer product would exhibit efficacy in the treatment of ulcerative colitis and decrease the incidence of side effects known with conventional monomeric equivalents.

We claim:

1. A polymeric compound which comprises a pharmacologically acceptable organic polymer backbone comprising a plurality of aromatic rings and having a molecular size which precludes the backbone's absorption from the intestinal lumen and a plurality of salicylic acid or salicylate salt groups covalently bonded to said backbone via azo groups that are intermediate backbone aromatic carbons and salicylic acid or salicylate salt 5-position carbons.

2. The compound of claim 1 wherein said backbone has an average molecular weight which is not less than 1000 daltons.

3. The compound of claim 1 wherein said plurality of aromatic rings is 10 or greater and said plurality of salicylic acid groups is 5 or greater.

4. The compound of claim 3 wherein said aromatic rings are pendant from an organic chain which links them together into the polymer backbone.

5. The compound of claim 3 wherein said aromatic rings are present as integral structural units in the organic backbone chain.

6. The compound of claim 3 wherein said backbone is polystyrene and said compound comprises recurring structural units of the formula

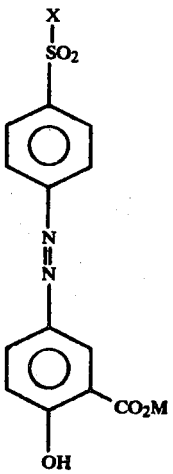

wherein M is hydrogen or a pharmacologically acceptable cation.

7. The compound of claim 3 having recurring units of the structure

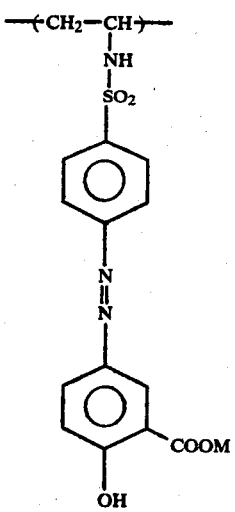

wherein M is hydrogen or a pharmacologically acceptable cation.

8. The compound of claim 7 wherein M is selected from among hydrogen, potassium and sodium.

9. The compound of claim 3 having recurring units of the structure wherein X is an amine group present in poly(ethyleneimine) and M is hydrogen or a pharmacologically acceptable cation.

10. The compound of claim 9 wherein M is selected from among hydrogen, sodium and potassium.

* * * * *